United States Patent [19]
Krantz

[11] Patent Number: 5,336,219
[45] Date of Patent: Aug. 9, 1994

[54] SKIN CLOSURE SYSTEM

[75] Inventor: Kermit E. Krantz, Mission Hills, Kans.

[73] Assignee: Medi-Flex Hospital Products, Inc., Overland Park, Kans.

[21] Appl. No.: 36,055

[22] Filed: Mar. 23, 1993

[51] Int. Cl.$^5$ ............................................. A63B 17/00
[52] U.S. Cl. ................................ 606/15; 606/216; 606/213
[58] Field of Search ............... 606/214, 215, 216, 213

[56] References Cited

U.S. PATENT DOCUMENTS

| | | | |
|---|---|---|---|
| 2,018,517 | 10/1935 | Fetter | 606/215 |
| 3,113,568 | 12/1963 | Robins | 606/215 X |
| 3,520,306 | 7/1970 | Gardner et al. | 606/215 |
| 4,531,521 | 7/1985 | Haverstock | 606/215 |
| 4,742,826 | 5/1988 | McLorg | 606/215 |
| 4,780,168 | 10/1988 | Beisang et al. | 606/215 X |
| 4,966,605 | 10/1990 | Thieler | 606/216 X |

*Primary Examiner*—Peter A. Aschenbrenner
*Attorney, Agent, or Firm*—Hovey, Williams, Timmons & Collins

[57] ABSTRACT

A skin closure system includes an elongated bandage provided with a fabric layer formed of relatively thick, pliable material and a support layer formed of relatively thin, stiff material. An intermediate adhesive layer is provided between the support layer and the fabric layer for securing them together, and an exposed adhesive layer is provided on the fabric layer opposite the support layer. An elongated strip of backing material is retained on the exposed adhesive layer of the bandage and is removable from the exposed adhesive layer to allow application of the bandage to the skin.

9 Claims, 2 Drawing Sheets

Fig.4.
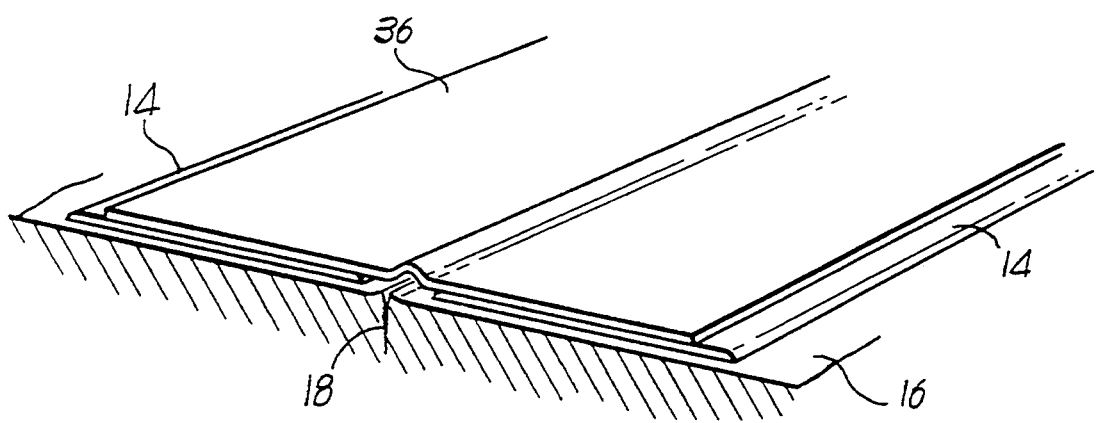
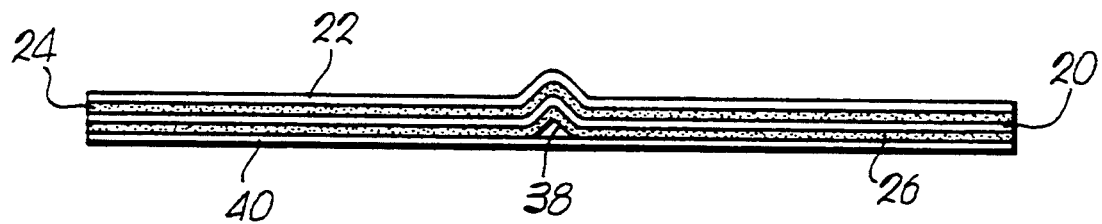
Fig.5.

SKIN CLOSURE SYSTEM

BACKGROUND OF THE INVENTION

1. Field of the Invention

The present invention relates generally to skin closure systems and, more particularly, to a system for closing a surgical incision or wound, wherein an elongated bandage is provided which is laid along the length of and bridges the incision to hold the edges of the incision together during healing.

2. Discussion of the Prior Art

It is known to provide a skin closure system comprising a device which is adhered to the skin prior to surgery along the line of an incision to be made. During surgery, the incision is made through the device so that two adjacent sheet portions of the device are defined, one on either side of the incision. One of these portions is provided with a flap that is folded back initially along the line on which the incision is to be made so that, upon completion of surgery, the flap may be unfolded, pulled across the incision, and adhered to the other portion to close the skin.

Alternately, it is known to provide skin closure systems which include staples or strips of adhesive bandage material which are applied to the skin in a direction transverse to the length of the incision, similar to stitches, in an attempt to pull the edges of the incision together and support the skin during healing.

It is possible to employ an adhesive with any of the foregoing systems for improving adherence between the device or bandage and the skin to be closed. For example, pressure-sensitive silicone adhesive is commercially available within a carrier which permits application of the adhesive to the skin around the incision, and the adhesive provides both a mechanical and chemical bond with any adhesive provided on the bandage or device to improve the adherence thereof with the skin.

Numerous problems arise through the use of conventional systems. For example, even when a conventional system employs strips of material adhered to the skin along the entire length of the incision, the means for bridging the incision does not support the incision during movement of the skin on a bias, e.g. when the patient twists in such a way as to form wrinkles in the skin that extend in a direction diagonal to the incision.

OBJECTS AND SUMMARY OF THE INVENTION

It is an object of the present invention to provide a skin closure system which adheres to and moves with the skin on both sides of an incision, while supporting the skin and holding the edges of the incision together even when the skin is pushed or pulled on a bias to the length of the incision.

It is another object of the present invention to provide a bandage which immobilizes an incision and distributes tension across the width of the bandage at angles to the direction of the force, as dictated by a fabric layer provided within the bandage.

Another object of the present invention is to provide a bandage which yields to folding of the skin during body movement while holding the edges of the incision together. Also, it is an object to provide a bandage which is transparent, allowing monitoring of the incision while presenting a bacterial barrier which impedes infection of the closed skin.

In accordance with these objects, and others which are evident from the following detailed description of a preferred embodiment, the invention relates to a skin closure system comprising a primary bandage including a fabric layer formed of an elongated strip of relatively thick, pliable material presenting opposed surfaces, and a support layer formed of an elongated strip of relatively thin, stiff material. An intermediate adhesive layer is provided between the support layer and one surface of the fabric layer for securing them together, and an exposed adhesive layer is provided on the opposed surface of the fabric layer. An elongated strip of backing material is retained on the exposed adhesive layer of the primary bandage and is removable from the exposed adhesive layer to allow application of the bandage to the skin.

According to one construction of the invention, the system includes a secondary bandage similar to the primary bandage, except that the secondary bandage is wider than the primary bandage and is provided with a pair of elongated strips of backing material rather than a single strip. Each of the strips of backing material are retained beside one another on the exposed adhesive layer of the secondary bandage and are independently removable from the secondary bandage. By providing this construction, one of the strips of backing material may be removed to allow application of the secondary bandage across from the primary bandage along the skin to be closed, and the other strip may then be removed to allow the secondary bandage to be adhered to the primary bandage across the skin to be closed.

In accordance with another aspect of the invention, the primary bandage may be provided with a generally centrally located, longitudinally extending ridge defining a concave channel in the exposed adhesive layer. In addition, the elongated strip of backing material is retained on the exposed adhesive layer of the primary bandage on both lateral sides of the channel but not within the channel.

Both of these bandage constructions are preferably employed in connection with a silicone adhesive that is applied to the skin surrounding the incision prior to application of the bandage. By employing such an adhesive, any moisture surrounding the incision is removed from the area, and improved adhesion is ensured between the bandage and the skin.

BRIEF DESCRIPTION OF THE DRAWING FIGURES

A preferred embodiment of the present invention is described in detail below with reference to the attached drawing figures, wherein:

FIG. 4 is a perspective view of a completed skin closure system constructed in accordance with a second preferred embodiment of the invention; and FIG. 5 is an end elevational view of the bandage of the second embodiment.

None of the elements illustrated in the figures are shown in proper proportion to one another, but have been distorted significantly in order to illustrate the various aspects of the invention as described in the following detailed description.

DETAILED DESCRIPTION OF THE PREFERRED EMBODIMENTS

Figure 2:
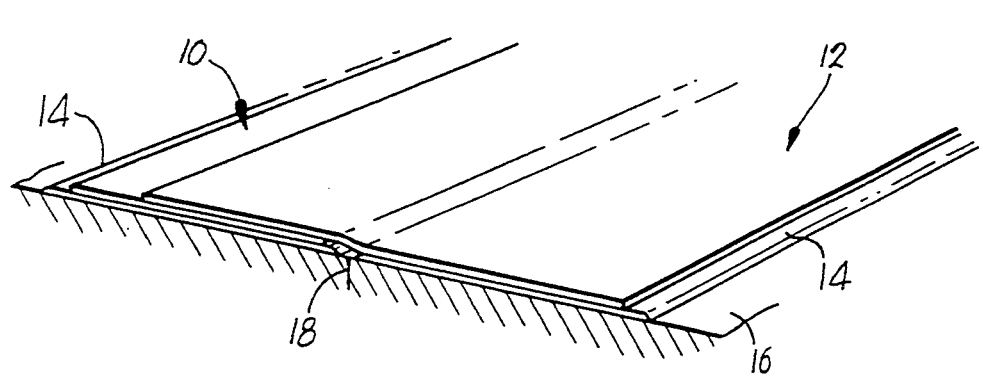
FIG. 2 is a perspective view of the completed skin closure system illustrated in FIG. 1.

A first preferred embodiment of a skin closure system constructed in accordance with the present invention is illustrated in FIG. 2, and broadly includes a primary bandage 10, a secondary bandage 12, and an adhesive 14 provided between the skin 16 and the bandages.

During use, when it is desired to close the skin along an incision or wound 18, the adhesive 14 is first applied directly to the skin within the area surrounding the incision. Preferably, the adhesive 14 is a pressure-sensitive silicone adhesive which adheres to the skin, even in the presence of moisture, and which dehydrates the area to improve adhesion of the bandages 10, 12. This is an important step in applying the skin closure system since the area surrounding a surgical incision is almost always moist, and such moisture impedes adherence of many conventional types of adhesives, such as gum-based adhesives or the like.

One particular type of silicone adhesive which may be used with the inventive system is packaged in a single-use, swab-tipped applicator, and is marketed under the tradename DERMASTIK by Medi-Flex Hospital Products, Inc. This product includes a medical adhesive, such as the 355 Medical Adhesive marketed by Dow Corning, which is provided in solution with a suitable carrier for permitting application of the adhesive to the skin. The carrier of this commercially available product is the solvent trichlorotrifluoroethane.

Once the adhesive 14 has been applied to the skin, the primary bandage 10 is pressed to the skin on top of the adhesive along one edge of the incision 18 and the secondary bandage 12 is pressed to the skin on top of the adhesive along the opposite edge of the incision. Thereafter, a portion of the secondary bandage is laid over the incision and adhered to the primary bandage, bridging the incision and adhering to the skin between the primary bandage and the secondary bandage.

Figure 3:
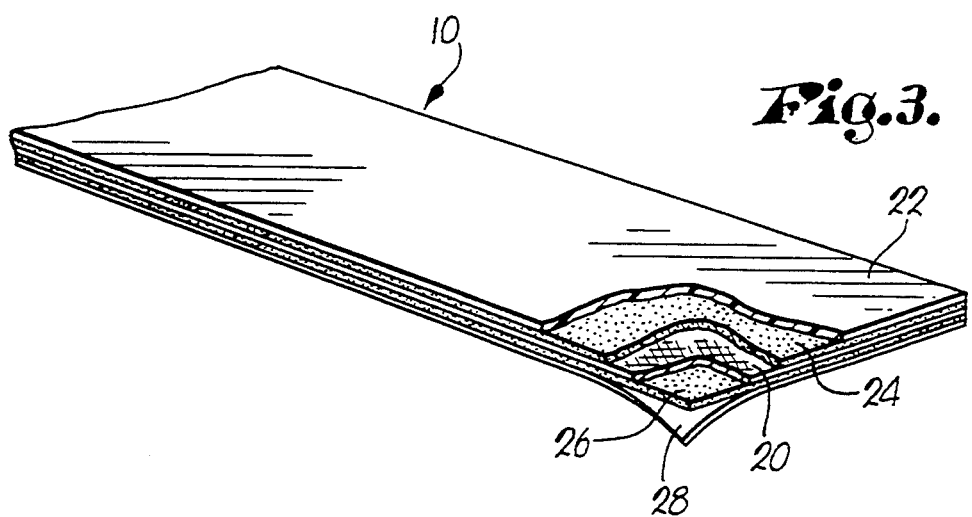
FIG. 3 is a perspective view of a bandage constructed in accordance with the first preferred embodiment, partially broken away to illustrate the layers of the bandage.

A primary bandage 10 constructed in accordance with the first preferred embodiment is illustrated in FIG. 3, and includes a fabric layer 20, a support layer 22, an intermediate adhesive layer 24 between the support layer and one surface of the fabric layer for securing them together, and an exposed adhesive layer 26 on the opposed surface of the fabric layer. Preferably, the primary bandage 10 is provided in 15 inch long strips, having a width of approximately one inch. A strip of backing material 28 is retained on the exposed adhesive layer 26 of the primary bandage and is removable from the exposed adhesive layer to allow application of the bandage to the skin.

The fabric layer 20 is formed of netting material that is thick and pliant relative to the support layer 22. The netting material preferably includes a boss-type, nonwoven fabric having a thickness of between 1–5 mils, and preferably between 4–5 mils. If the fabric layer is too thick, the bandage will not move with the skin during movement thereof on a bias, e.g. when the patient twists in such a way as to form wrinkles in the skin that extend in a direction diagonal to the incision. Instead, the bandage will resist the natural folding of the skin, increasing the shear between the edges of the incision and allowing reopening of the wound.

An example of a preferred material for use in the fabric layer 20 is marketed by Applied Extrusion Technologies, Inc., as DELNET P530 nonwoven fabric, having a thickness of 4.4 mils, a weight of 0.62 oz/yd$^2$, a boss count of 22 in the longitudinal direction of the strip and of 36 in the lateral direction of the strip, and being formed of high density polyethylene (HDPE).

The support layer 22 is formed of a transparent film having a thickness less than the thickness of the fabric layer, and which is stiffer than the netting material of the fabric layer. Preferably, the film is formed of polyurethane, having a thickness of about 1 mil or less, and allows moisture to be transmitted through the film while reducing the opportunity for bacteria to pass through the bandage to the closed skin. If the support layer is too thick, the stiffness of the film obviates the advantage provided by the fabric, reducing the ability of the bandage to move with the closed skin.

The intermediate adhesive layer 24 covers the entire area of the support layer 22 so that the fabric layer and support layer are secured together in complete surface-to-surface contact, with each layer supporting the other. Thus, the support layer 22 gives strength to the fabric layer 20 and prevents the fabric layer from being stretched excessively, while the fabric layer and intermediate adhesive layer contribute pliancy to the support layer, enabling the bandage to move with the skin, even when the skin wrinkles or folds during movement on a bias to the incision.

An example of a preferred film for use as the support layer 22 is marketed by Avery as a MED 5020 Polyurethane Film, that consists of a transparent, 1 mil thick polyurethane film coated with a nonsensitizing acrylic copolymer pressure-sensitive adhesive which is protected by a white, densified kraft paper with a silicone release coating on one side. Thus, the intermediate adhesive layer 24 is provided on the film prior to construction of the bandage, and serves to hold the fabric layer against the support layer in the final bandage construction. The adhesive is provided on the film in an amount of 50 grams/m$^2$.

The exposed adhesive layer 26 is also preferably comprised of a nonsensitizing acrylic copolymer adhesive which is applied to the surface of the fabric layer 20 which is opposite the support layer. Preferably, the exposed adhesive layer is provided on the fabric layer in an amount of 42 grams/m$^2$. An exemplary adhesive is marketed by Avery as MED 1118 Transfer Tape, and includes the acrylic copolymer supported on a semi-bleached kraft release liner coated on two sides with a silicone release coating. However, any firm, stable acrylic adhesive may be used which adheres aggressively to skin without causing irritation.

The elongated strip of backing material 28 is preferably formed of densified kraft paper having a silicone release coating on one surface thereof. The backing layer, as well as all other layers of the primary bandage, is of the same length and width as the remaining layers so that when the backing layer is removed from the bandage, the entire bandage may be adhered to the skin along an edge of the incision to be closed.

Although not shown, the bandage may be provided with a tab at one end thereof for permitting easy removal of the backing material from the bandage. Preferably, this tab is formed by providing a small piece of kraft paper between the exposed adhesive layer and the strip of backing material along a short length of the bandage at one end thereof. This small piece of kraft paper adheres to the exposed adhesive layer and prevents the backing material from sticking to the bandage in the area of the tab so that the backing material may be gripped within this area and pulled from the bandage.

Figure 1:
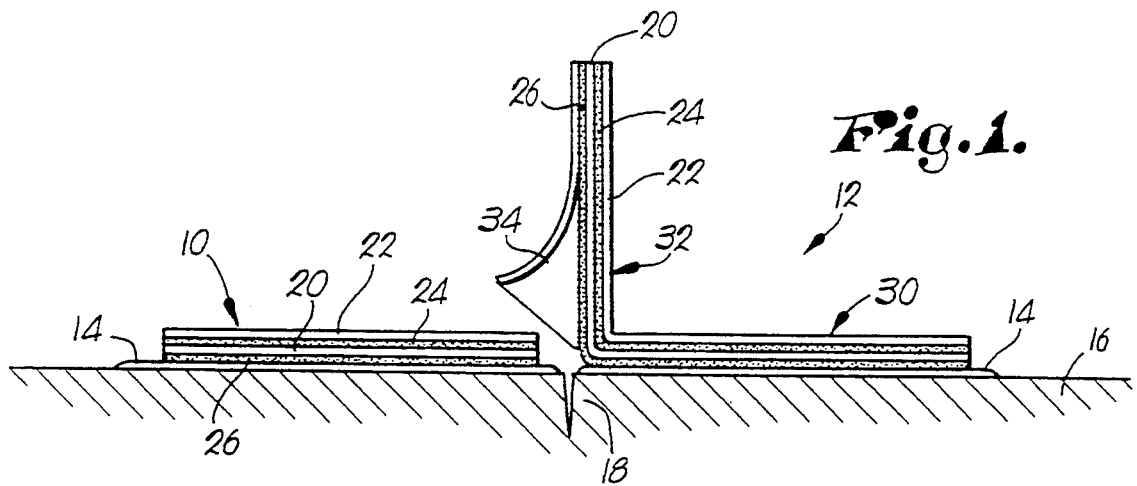
FIG. 1 is an end elevational view of a skin closure system constructed in accordance with a first embodiment of the present invention, illustrating the method of applying the system to the skin.

The secondary bandage 12 is illustrated in FIG. 1, and is identical to the primary bandage 10 except that it is wider than the primary bandage, the secondary bandage preferably being just less than twice the width of the primary bandage. Although the secondary bandage is formed of a single strip of material, two laterally spaced, longitudinally extending portions 30, 32 are defined by the strip, one of which is a body portion 30 having a width substantially equal to the width of the primary bandage 10, and the other of which is a bridging portion 32 having a smaller width. During construction of the secondary bandage, these portions 30, 32 may be formed by partially scoring or folding the strip along the line separating the portions.

An elongated strip of backing material identical to the strip 28 is retained on the exposed adhesive layer of the body portion 30 and is removable from the secondary bandage 12 to permit the body portion of the secondary bandage to be adhered to the skin along an edge of the incision to be closed, opposite the primary bandage 10.

An additional strip 34 of backing material is retained on the exposed adhesive layer 26 of the bridging portion 32 of the secondary bandage and is retained on the bandage when the backing material is removed from the body portion. Thus, the exposed adhesive layer of the bridging portion 32 remains covered while the body portion of the secondary bandage is adhered to the skin, and the backing material 34 provided on the bridging portion may then be removed to allow the bridging portion to be laid across the incision over the primary bandage so that it may be pressed against the primary bandage and adhered thereto.

As with the primary bandage 10, a tab is provided on the secondary bandage 12 to permit easy removal of the two strips of backing material.

A bandage 36 constructed in accordance with a second preferred embodiment of the invention is illustrated in FIG. 5, and is identical to the primary bandage 10, except that the bandage 36 is about twice as wide as the primary bandage 10. The layers 20, 22, 24, 26 of the bandage 36 are numbered to indicate the same layers as are present in the primary and secondary bandages of the preceding embodiment.

The bandage 36 is constructed differently than the primary bandage 10 in that a generally centrally located, longitudinally extending ridge is defined in the bandage. This ridge is of concavo-convex shape when viewed in FIG. 5, such that a concave channel 38 is defined by the exposed adhesive layer 26, the channel being adapted to be aligned with the incision 18 when the bandage is adhered to the skin to be closed.

A strip of backing material 40 is retained on the exposed adhesive layer 26 on both lateral sides of the channel 38, but does not contact the adhesive layer within the channel. Thus, the backing material supports the layers of the bandage to maintain the channel within the bandage until the backing material is removed. However, because of the supple character of the bandage, the bandage naturally returns toward a flat strip shape when the backing material is removed.

As with the primary bandage 10, a tab is provided on the bandage to permit easy removal of the backing material.

With reference to FIG. 4, after the silicone adhesive 14 has been applied to the skin 16 surrounding the incision 18, and the backing material 40 has been pulled from the bandage 36 along a portion of the length of the bandage extending inward from the tab, the bandage is pressed against the adhesive 14 over the skin to be closed with the channel 38 aligned with the incision. Simultaneously, the edges of the incision are pressed toward one another and are raised slightly, and the bandage is pressed onto the skin with the raised edges of the incision extending into the channel of the bandage. After the bandage has been adhered to the skin, the bandage assumes a flat cross-sectional shape and the edges of the incision recede to the level of the surrounding skin so that a continuous width of bandage extends across and covers the incision while supporting the incision against reopening.

In order to apply the bandage in accordance with this method, it is possible to provide an applicator having a surface shaped like the bandage 36, with a longitudinal groove formed therein, so that when the applicator is moved along the incision, it presses the skin surrounding the incision down, forcing the edges to be raised toward one another. At the same time, the applicator presses the bandage against the skin with the channel aligned over the incision.

By providing a skin closure system in accordance with the present invention, numerous advantages are realized. For example, by providing a bandage or bandages of the previously described construction, the system breathes to provide a relatively high moisture vapor transmission rate such that excess moisture in and around the incision may pass through the system. This increases the comfort of the system and enables the bandage to remain in place for longer periods of time than in conventional systems.

In addition, by employing transparent fiber, support and adhesive layers, application of the bandage is simplified, and it is possible to monitor healing of the closed skin. This enables a physician to determine whether primary closure is achieved, as well as allowing early detection of hematoma or of erythema which might indicate infection.

The system also presents a barrier to bacteria which impedes the opportunity for infection of the closed skin and acts as a shield against physical contact with the closed skin.

More importantly, by employing a bandage constructed in accordance with the present invention, it is possible to immobilize the incision and to distribute tension across the width of the bandage at angles dictated by the boss distribution within the netting material of the bandage. In addition, the bandage yields with the skin when the skin folds and twists during natural body movement, but holds the edges of the incision together even when the skin moves on a bias or on a diagonal to the incision. The bandage also spreads tension along the entire edge of the incision, rather than being localized as is the case with conventional staples, strips or the like.

Although the invention has been described with reference to the preferred embodiment illustrated in the drawing figures it is understood that substitutions may be made and equivalents employed herein without departing from the scope of the invention as recited in the claims.

What is claimed is:

1. A skin closure system comprising:

a primary bandage including a fabric layer formed of a first material having a thickness of about 1–5 mils and presenting opposed surfaces, a support layer formed of an elongated strip of a second material, an intermediate adhesive layer between the support layer and one surface of the fabric layer for securing them together, and an exposed adhesive layer on the opposed surface of the fabric layer, the support layer having a thickness less than the thickness of the fabric layer and being inflexible relative to the first material; and an elongated strip of backing material that is retained on the exposed adhesive layer of the primary bandage and is removable from the exposed adhesive layer to allow application of the bandage to the skin.

2. A skin closure system as recited in claim 1, wherein the fabric layer is a netting formed of high density polyethylene (HDPE).

3. A skin closure system as recited in claim 2, wherein the fabric layer is about 4.4 mils thick.

4. A skin closure system as recited in claim 1, wherein the support layer is a film of polyurethane having a thickness of about 1 mil or less.

5. A skin closure system as recited in claim 1, wherein the intermediate and exposed adhesive layers are formed of a nonsensitizing acrylic copolymer.

6. A skin closure system as recited in claim 1, wherein the backing material is kraft, and is provided with a coating of silicone which permits the kraft to be removed from the exposed adhesive layer.

7. A skin closure system as recited in claim 1, further comprising a secondary bandage which also includes a fabric layer formed of an elongated strip of relatively thick, pliable material presenting opposed surfaces, a support layer formed of an elongated strip of relatively thin, stiff material, an intermediate adhesive layer between the support layer and one surface of the fabric layer for securing them together, and an exposed adhesive layer on the opposed surface of the fabric layer; and a pair of elongated strips of backing material which are retained beside one another on the exposed adhesive layer of the secondary bandage and are independently removable from the secondary bandage so that one of the strips of backing material may be removed to allow application of the secondary bandage across from the primary bandage along the skin to be closed, and the other strip may then be removed to allow the secondary bandage to be adhered to the primary bandage across the skin to be closed.

8. A skin closure system as recited in claim 1, wherein the primary bandage includes a generally centrally located, longitudinally extending ridge defining a concave channel in the exposed adhesive layer, the strip of backing material being retained on the exposed adhesive layer of the primary bandage on both lateral sides of the channel but not within the channel.

9. A skin closure system as recited in claim 1, wherein the primary bandage is transparent.

* * * * *